United States Patent [19]

Böger et al.

[11] 4,232,011
[45] Nov. 4, 1980

[54] 1-PHOSPHORYLATED 2-(PHENOXYALKYL)-2-IMIDAZOLINE DERIVATIVES AND THEIR USE IN PEST CONTROL

[75] Inventors: Manfred Böger, Weil am Rhein, Fed. Rep. of Germany; Jozef Drabek, Oberwil, Switzerland; Günter Mattern, Liestal, Switzerland; Walter Traber, Reinach, Switzerland

[73] Assignee: Ciba-Geigy Corporation, Ardsley, N.Y.

[21] Appl. No.: 86,888

[22] Filed: Oct. 22, 1979

[30] Foreign Application Priority Data

Nov. 2, 1978 [CH] Switzerland ..................... 11291/78
Jun. 8, 1979 [CH] Switzerland ..................... 5367/79

[51] Int. Cl.³ .................... A01N 57/32; C07F 9/65
[52] U.S. Cl. .................................. 424/200; 548/111; 548/353
[58] Field of Search ................... 548/111; 424/200

[56] References Cited
FOREIGN PATENT DOCUMENTS 51-106739  9/1976  Japan .
472941     3/1976  U.S.S.R. .

OTHER PUBLICATIONS

Prokof'eva et al, Chem. Abst., 1977, vol. 87, No. 102232r.

Primary Examiner—Alan L. Rotman
Assistant Examiner—Natalie Harkaway
Attorney, Agent, or Firm—John J. Maitner

[57] ABSTRACT

Compounds of the formula I

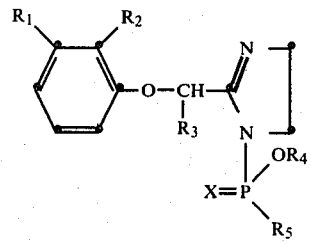

wherein $R_1$ and $R_2$ are each methyl or chlorine, $R_3$ is hydrogen or $C_1$–$C_4$-alkyl, $R_4$ is methyl or ethyl, $R_5$ is methoxy, ethoxy, $C_1$–$C_4$-alkylthio or phenyl and X is oxygen or sulphur have valuable pesticidal in particular acaricidal properties.

12 Claims, No Drawings

1-PHOSPHORYLATED 2-(PHENOXYALKYL)-2-IMIDAZOLINE DERIVATIVES AND THEIR USE IN PEST CONTROL

The present invention relates to novel 1-phosphorylated 2-(phenoxy-alkyl)-2-imidazoline derivatives which are effective against pests, a process for their manufacture, pesticidal compositions which contain these derivatives as active component, and a method of controlling pests which comprises the use of the novel compounds.

2-(Phenoxyalkyl)-2-imidazolines having pesticidal, especially ectoparasiticidal, action are known (cf. for example South African patent application No. 78/2449, Japanese published patent specification No. 76/106739 and German Offenlegungsschrift No. 2 756 639). The present invention provides novel compounds of this type which also are effective against pests, especially against representatives of the order Acarina, and which are particularly suitable for practical use because of their advantageous biological properties.

The 1-phosphorylated 2-(phenoxyalkyl)-2-imidazoline derivatives of the present invention have the formula

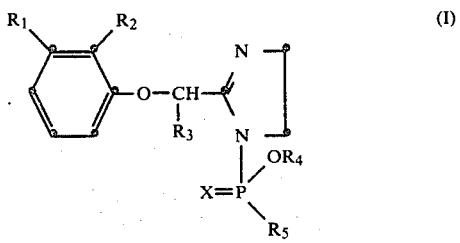

wherein $R_1$ and $R_2$ are each independently chlorine or methyl, $R_3$ is hydrogen or $C_1$–$C_4$ alkyl, $R_4$ is methyl or ethyl, $R_5$ is methoxy, ethoxy, $C_1$–$C_4$ alkylthio or phenyl, and X is oxygen or sulfur.

Within the scope of formula I, $C_1$–$C_4$ alkyl is to be understood as meaning methyl, ethyl, n-propyl and isopropyl, as well as n-butyl, isobutyl, sec- and tert-butyl. Such alkyl groups also form the alkyl moiety of $C_1$–$C_5$ alkylthio groups represented by $R_5$.

In the compounds of formula I, the following types of substituents and combinations thereof are preferred:
(1) for $R_3$: hydrogen, methyl and ethyl, especially ethyl;
(2) for $R_4$: ethyl;
(3) for $R_5$: n-propylthio, isobutylthio and sec-butylthio;
(4) for X: oxygen.

The compounds of formula I also exist in the form of acid addition salts, e.g. mineral acid salts, and can be used in the form of their salts in accordance with the invention. Accordingly, the invention is to be construed as comprising both the free compounds of formula I and their acid addition salts.

The present invention is based on the surprising observation that the compounds of formula I are very effective both against plant-destructive acarids (mites e.g. of the families Tetranychidae, Tarsonemidae, Eriophyidae, Tyroglyphidae and Glycyphagidae) and against ectoparasitic acarids (mites and ticks e.g. of the families Ixodidae, Argasidae, Sarcoptidae and Dermanyssidae) which are harmful to productive livestock.

In addition, it has been observed that, when applied to plants, the compounds of formula I have the property of penetrating the surface of the leaves into the interior. Because of these properties, the compounds of formula I and their non-toxic acid addition salts are particularly suitable for controlling pests that damage plants by sucking, especially phytoparasitic acarids, in crops of useful plants and ornamentals, especially in crops of fruit and vegetables and, most particularly, in crops of citrus fruit.

The compounds of formula I are obtained by methods analogous to known ones, for example by reacting a compound of formula II

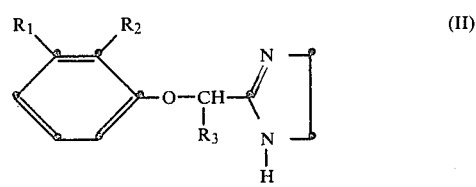

in the presence of a base, with a compound of the formula III

in which formulae II and III above the symbols $R_1$, $R_2$, $R_3$, $R_4$ and $R_5$ are as defined for formula I and Hal is a halogen atom, in particular a chlorine or bromine atom.

The process is advantageously carried out in the temperature range between $-20°$ and $+80°$ C., under normal or slightly elevated pressure, and preferably in the presence of a solvent or diluent which is inert to the reactants.

Examples of suitable solvents or diluents are ethers and ethereal compounds, such as diethyl ether, diisopropyl ether, dioxane and tetrahydrofurane; aromatic hydrocarbons, such as benzene, toluene and xylenes; ketones, such as acetone, methyl ethyl ketone and cyclohexanone.

Suitable bases for this process are in particular tertiary amines, such as trialkylamines, pyridines and dialkyl anilines, and hydroxides, oxides, carbonates and bicarbonates of alkali metal and alkaline earth metal alcoholates, e.g. potassium tert-butylate and sodium methylate.

The compounds of formula I so obtained can be converted into their acid addition salts by methods which are known per se.

The compounds of formula I, wherein $R_3$ is alkyl, exist in the form of optically active isomers. Accordingly, racemic mixtures are obtained if no optically active starting materials are employed in the manufacture of these compounds. Such mixtures of isomers can be separated into the individual isomers, e.g. by chromatographic separating methods. The invention is to be construed as comprising both the individual optically active isomers and mixtures thereof.

The starting materials employed in the above process are known (cf. South African patent application No. 78/2449 and German Offenlegungsschrift No. 2 756 638) or they can be obtained by methods analogous to known ones.

The compounds of formula I are employed in this invention as pure active substance or they form a constituent of compositions which additionally contain suitable carriers or adjuvants or mixtures thereof.

Suitable carriers and adjuvants can be solid or liquid and correspond to the substances conventionally used in the art of formulation, e.g. natural or regenerated substances, solvents, dispersing agents, wetting agents, tackifiers, thickeners, binders and/or fertilisers.

The acaricidal action of the compositions of the invention can be substantially broadened by addition of other acaricides and/or insecticides. Examples of suitable additives are: organophosphorus compounds, nitrophenols and derivatives thereof, formamidines, ureas, pyrethroids, carbamates, and chlorinated hydrocarbons.

The compositions of the invention can be formulated e.g. as dusts, granulates, dispersions, solutions and suspensions, and also as water-dispersible wettable powders, pastes, emulsions and emulsifiable concentrates. The content of active substance (compound of formula I) in the above compositions is between 0.1 and 95%, though higher concentrations can also be used if the compositions are applied from an aircraft or other appropriate application device.

The active substances of the formula I can be formulated e.g. as follows (throughout this specification, the parts are by weight):

Emulsifiable concentrate I 20 parts of active substance of the formula I are dissolved in 70 parts of xylene, and to this solution are added 10 parts of an emulsifying agent consisting of a mixture of an arylphenylpolyglycol ether and the calcium salt of dodecylbenzenesulfonic acid. The resultant emulsifiable concentrate can be diluted with water in any ratio to form a milky emulsion.

Emulsifiable concentrate II

With stirring, 5 to most 30 parts of active substance are dissolved at room temperature in 30 parts of dibutyl phthalate, 10 parts of Solvent 200 (low viscosity, highly aromatic petroleum distillate) and 15 to 35 parts of Dutrex 238 FC (viscous highly aromatic petroleum distillate). To this solution are added 10 parts of an emulsifier mixture consisting of castor oil polyglycol ether and the calcium salt of dodecylbenzenesulfonate. The resultant emulsifiable concentrate forms milky emulsions in water.

Wettable powder

The following ingredients are intensively mixed in a mixing apparatus: 5 to 30 parts of active substance, 5 parts of an absorbent carrier (silica gel K 320 or Wessalon S), 55 to 80 parts by weight of a carrier (Bolus alba or kaolin B 24) and a dispersing agent mixture consisting of 5 parts of a sodium laurylsulfonate and 5 parts of an alkylaryl polyglycol ether. This mixture is ground to a granular size of 5-15 μm in a disc attrition mill or air jet mill. The resultant wettable powder forms a good suspension in water.

Pour-on solution

A 100 ml pour-on solution is obtained as follows: With stirring, 30.0 g of active substance are dissolved in 48.0 g of benzyl alcohol, if necessary while heating gently. Then 3.0 g of sodium dioctylsulfosuccinate and 19.8 g of ground nut oil are added to the above solution and dissolved by heating and thorough stirring.

The invention is illustrated in more detail by the following Examples.

EXAMPLE 1

Manufacture of 1-(diethoxyphosphynyl)-2-[1-(2,3-dimethylphenoxy)-propyl]-2-imidazoline 6 g of triethylamine are added at 0° C. to a solution of 11.6 g of 2-[1-(2,3-dimethylphenoxy)-propyl]-2-imidazoline in 100 ml of toluene. With continuous stirring, 8.6 g of diethyl chlorophosphate are then added slowly dropwise at 0° to 10° C. The resultant suspension is stirred for a further 2 hours at room temperature, diluted with a small amount of water and the toluene phase is washed with a small amount of water. The toluene solution is dried and concentrated and the residue is dried in a high vacuum, affording 1-(diethoxyphosphynyl)-2-[1-(2,3-dimethylphenoxy)-propyl]-2-imidazoline of the formula

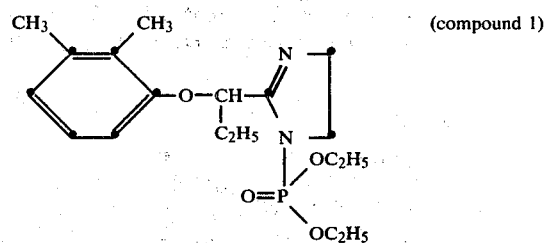

(compound 1)

in the form of a clear yellow oil with a refraction of $n_D^{20} = 1.5092$. The following compounds of the formula I

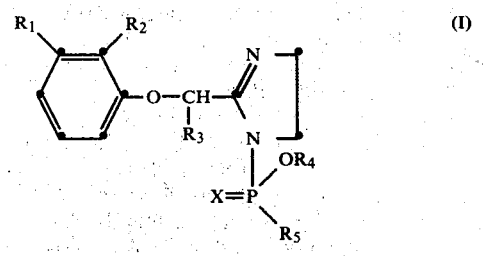

(I)

can be obtained in analogous manner:

| Compound | $R_1$ | $R_2$ | $R_3$ | $R_4$ | $R_5$ | X | Physical data |
|---|---|---|---|---|---|---|---|
| 2 | $CH_3$ | $CH_3$ | H | $CH_3$ | $CH_3O$ | O | m.p. 147–149° C. |
| 3 | $CH_3$ | $CH_3$ | H | $C_2H_5$ | $C_2H_5O$ | O | $n_D^{20}$:1.5126 |
| 4 | $CH_3$ | $CH_3$ | H | $C_2H_5$ | $C_2H_5S$ | O | $n_D^{20}$:1.5527 |
| 5 | $CH_3$ | $CH_3$ | H | $C_2H_5$ | ⌬ | S | $n_D^{20}$:1.5960 |
| 6 | $CH_3$ | $CH_3$ | H | $C_2H_5$ | (n)$C_3H_7S$ | O | $n_D^{20}$ 1.5431 |
| 7 | $CH_3$ | $CH_3$ | H | $C_2H_5$ | (n)$C_3H_7S$ | S | $n_D^{20}$:1.5152 |
| 8 | $CH_3$ | $CH_3$ | H | $C_2H_5$ | (s)$C_4H_9S$ | O | $n_D^{20}$:1.5421 |
| 9 | $CH_3$ | $CH_3$ | H | $C_2H_5$ | (i)$C_4H_9S$ | O | |
| 10 | $CH_3$ | $CH_3$ | $CH_3$ | $C_2H_5$ | (n)$C_3H_7S$ | O | |
| 11 | $CH_3$ | $CH_3$ | $C_2H_5$ | $CH_3$ | $CH_3O$ | O | $n_D^{20}$:1.5231 |
| 12 | $CH_3$ | $CH_3$ | $C_2H_5$ | $C_2H_5$ | $C_2H_5S$ | O | $n_D^{20}$:1.5399 |
| 13 | $CH_3$ | $CH_3$ | $C_2H_5$ | $C_2H_5$ | ⌬ | S | $n_D^{20}$:1.5821 |
| 14 | $CH_3$ | $CH_3$ | $C_2H_5$ | $C_2H_5$ | (n)$C_3H_7S$ | O | $n_D^{20}$ 1.5341 |
| 15 | $CH_3$ | $CH_3$ | $C_2H_5$ | $C_2H_5$ | (n)$C_3H_7S$ | S | $n_D^{20}$:1.5609 |

-continued

| Compound | R₁ | R₂ | R₃ | R₄ | R₅ | X | Physical data |
|---|---|---|---|---|---|---|---|
| 16 | CH₃ | CH₃ | C₂H₅ | C₂H₅ | (s)C₄H₉S | O | $n_D^{20}$:1.5314 |
| 17 | CH₃ | CH₃ | C₂H₅ | C₂H₅ | (i)C₄H₉S | O | $n_D^{20}$:1.5306 |
| 18 | Cl | Cl | C₂H₅ | CH₃ | CH₃O | O | |
| 19 | Cl | Cl | C₂H₅ | C₂H₅ | C₂H₅O | O | |
| 20 | Cl | Cl | C₂H₅ | C₂H₅ | C₂H₅S | O | |
| 21 | Cl | Cl | C₂H₅ | C₂H₅ | ⌬ | S | |
| 22 | Cl | Cl | C₂H₅ | C₂H₅ | (n)C₃H₇S | O | |
| 23 | Cl | Cl | C₂H₅ | C₂H₅ | (n)C₃H₇S | S | |
| 24 | Cl | Cl | C₂H₅ | C₂H₅ | (s)C₄H₉S | O | |
| 25 | Cl | Cl | C₂H₅ | C₂H₅ | (i)C₄H₉S | O | |
| 26 | Cl | CH₃ | (n)C₄H₉ | C₂H₅ | (s)C₄H₉S | O | $n_D^{20}$:1.5235 |
| 27 | Cl | CH₃ | (n)C₃H₇ | C₂H₅ | (s)C₄H₉S | O | $n_D^{20}$:1.5258 |
| 28 | Cl | CH₃ | CH₃ | C₂H₅ | (s)C₄H₉S | O | $n_D^{20}$:1.5380 |

EXAMPLE 2

Action against plant-destructive acarids (mites) *Tetranychus urticae* (OP-sensitive) and *Tetranychus cinnabarius* (OP-tolerant)

The primary leaves of *Phaseolus vulgaris* plants were infected with a infested piece of leaf from a mass culture of *Tetranychus urticae* (OP-sensitive) or *Tetranychus cinnabarius* (OP-tolerant). (The tolerance refers to the tolerance to diazinone). The treated, infested plants were sprayed dripping wet with a test solution containing 400 or 200 ppm of the compound to be tested. The number of living and dead imagines and larvae (all mobile stages) was evaluated under a stereoscopic microscope after 24 hours and again after 7 days. One plant was used for each test substance and test species. During the test run, the plants stood in greenhouse compartments at 25° C.

In the above test, the compounds of formula I were effective against adults and larvae of the species *Tetranychus urticae* and *Tetranychus cinnabarius*.

EXAMPLE 3

Action against ectoparasitic acarids (ticks: *Rhipicephalus bursa* (imagines and larvae), *Amblyomma hebraeum* (♀ imagines, nymphs and larvae) and *Boophilus microplus* (larvae, OP-sensitive and OP-tolerant)

The test organisms employed were about 50 larvae, about 25 nymphs or about 10 imagines of each of the tick species *Rhipicephalus bursa*, *Amblyomma hebraeum* and *Boophilus microplus*. The test organisms were immersed briefly in an aqueous emulsion or solution containing 0.1, 1.0, 10, 50 or 100 ppm of the respective compound. The emulsions or solutions in test tubes were then absorbed by cotton wool and the wetted test organisms were kept in the contaminated tubes. Evaluation of mortality at each concentration was made after 3 days (larvae) and 14 days (nymphs and imagines).

Compounds of the formula I were effective in this test against larvae, nymphs and imagines of *Rhipicephalus bursa* and *Amblyomma hebraeum* and against larvae (OP-resistant and OP-sensitive) of *Boophilus microplus*.

What is claimed is:

1. A compound of the formula I

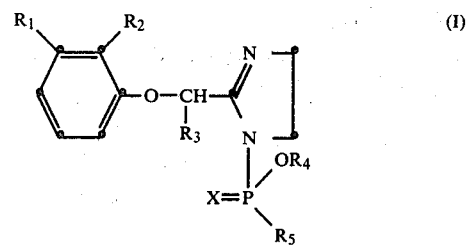

wherein R₁ and R₂ are each independently methyl or chlorine, R₃ is hydrogen or C₁-C₄-alkyl, R₄ is methyl or ethyl, R₅ is methoxy, ethoxy, C₁-C₄-alkylthio or phenyl and X is oxygen or sulphur.

2. A compound as claimed in claim 1 wherein R₄ is ethyl and R₅ is n-propylthio, i-butylthio or s-butylthio.

3. A compound as claimed in claim 1 or 2 wherein R₃ is hydrogen, methyl or ethyl.

4. A compound as claimed in claim 3 wherein R₃ is ethyl.

5. A compound as claimed in claim 3 wherein X is oxygen.

6. A compound as claimed in claim 1 of the formula

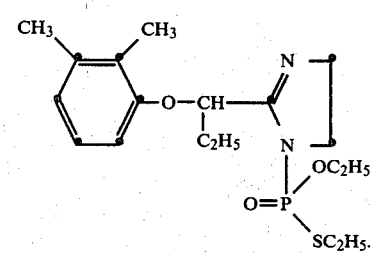

7. A compound as claimed in claim 1 of the formula

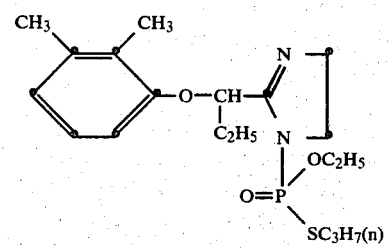

8. A compound as claimed in claim 1 of the formula

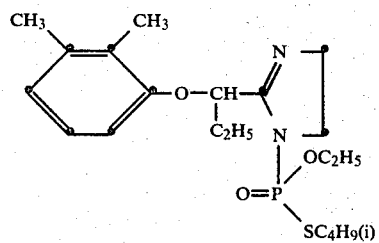

9. A compound as claimed in claim 1 of the formula

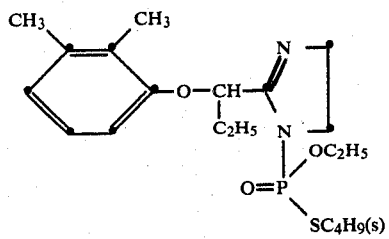

10. A pesticidal composition comprising a pesticidally effective amount of a compound as claimed in claim 1 together with an inert, solid or liquid diluent or carrier therefor.

11. A method of controlling pests at a locus, which method comprises applying to said locus a pesticidally effective amount of a compound as claimed in claim 1.

12. A method as claimed in claim 11 wherein the pests are pests of the order Acarina.

* * * * *